(12) United States Patent
Bassett et al.

(10) Patent No.: US 9,707,058 B2
(45) Date of Patent: Jul. 18, 2017

(54) PATIENT-SPECIFIC IMPLANTS WITH IMPROVED OSSEOINTEGRATION

(75) Inventors: Jeffrey A. Bassett, Vista, CA (US); Michael Collins, San Marcos, CA (US); Sean Cahill, Temecula, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 463 days.

(21) Appl. No.: 12/501,163

(22) Filed: Jul. 10, 2009

(65) Prior Publication Data

US 2011/0008754 A1    Jan. 13, 2011

(51) Int. Cl.
*A61C 8/00* (2006.01)
*A61F 2/28* (2006.01)
*A61L 27/08* (2006.01)
*A61L 27/30* (2006.01)
*A61L 27/56* (2006.01)
(Continued)

(52) U.S. Cl.
CPC .......... *A61C 8/0012* (2013.01); *A61C 8/0013* (2013.01); *A61F 2/2803* (2013.01); *A61L 27/08* (2013.01); *A61L 27/30* (2013.01); *A61L 27/56* (2013.01); *A61F 2/30942* (2013.01); *A61F 2002/30011* (2013.01); *A61F 2002/3092* (2013.01); *A61F 2002/30929* (2013.01); *A61F 2002/30952* (2013.01); *A61F 2002/30962* (2013.01); *A61F 2002/30981* (2013.01); *A61F 2250/0023* (2013.01); *A61F 2310/00161* (2013.01); *A61F 2310/00544* (2013.01); *A61L 2430/02* (2013.01); *B33Y 80/00* (2014.12); *Y10T 29/49568* (2015.01)

(58) Field of Classification Search
CPC ....... A61C 8/0013; A61C 8/0012; A61C 8/00; A61F 2002/30011; A61F 2310/00544; A61F 2/2803; A61F 2/30942; A61F 2002/3092; A61F 2002/30929; A61F 2002/30952; A61F 2002/30962; A61F 2002/30981; A61F 2250/0023; A61F 2310/00161; A61L 2430/02; A61L 27/56; A61L 27/08; A61L 27/30; Y10T 29/49568
USPC ..................... 433/174, 175, 173, 172, 201.1; 29/896.11
See application file for complete search history.

(56) References Cited

U.S. PATENT DOCUMENTS 2,721,387 A    10/1955  Ashuckian
3,314,420 A    4/1967   Smith et al.
(Continued)

FOREIGN PATENT DOCUMENTS

CA    2506854    7/2001
DE    4209569    11/1994
(Continued)

OTHER PUBLICATIONS

An Introduction to Silanes and Their Clinical Applications in Dentistry, Jukka P.I Matinlinna et al., vol. 17, No. 2, pp. 155-164 The International Journal of Prosthodontics, 2004.
(Continued)

*Primary Examiner* — Cris L Rodriguez
*Assistant Examiner* — Mirayda A Aponte
(74) *Attorney, Agent, or Firm* — Schwegman Lundberg & Woessner, P.A.

(57) ABSTRACT

A patient-specific bone implant has a porous body with a core material covered with tantalum. It is made with unique outer dimensions selected to match a specific patient.

17 Claims, 13 Drawing Sheets

(51) Int. Cl.
  *B33Y 80/00* (2015.01)
  *A61F 2/30* (2006.01)

(56) References Cited

U.S. PATENT DOCUMENTS

| | | | |
|---|---|---|---|
| 3,423,830 A | 1/1969 | Halpern et al. | |
| 3,423,831 A | 1/1969 | Semmelman | |
| 3,435,526 A | 4/1969 | Brancato | |
| 3,497,953 A | 3/1970 | Weissman | |
| 3,685,115 A | 8/1972 | Scott | |
| 3,713,860 A | 1/1973 | Auskern | |
| 3,740,851 A | 6/1973 | Weissman | |
| 3,797,113 A | 3/1974 | Brainin | |
| 3,849,887 A | 11/1974 | Brainin | |
| 3,855,638 A * | 12/1974 | Pilliar | 623/23.55 |
| 3,896,547 A | 7/1975 | Kulwiec | |
| 3,905,109 A | 9/1975 | Cohen et al. | |
| 3,906,550 A | 9/1975 | Rostoker | |
| 3,919,773 A | 11/1975 | Freeman | |
| 3,934,347 A | 1/1976 | Lash et al. | |
| 3,992,725 A | 11/1976 | Homsy | |
| 4,011,602 A | 3/1977 | Rybicki et al. | |
| 4,016,651 A | 4/1977 | Kawahara et al. | |
| 4,086,701 A | 5/1978 | Kawahara et al. | |
| 4,097,935 A | 7/1978 | Jarcho | |
| 4,122,605 A | 10/1978 | Hirabayashi et al. | |
| 4,131,597 A | 12/1978 | Bluethgen et al. | |
| 4,178,686 A | 12/1979 | Riess et al. | |
| 4,195,366 A | 4/1980 | Jarcho et al. | |
| 4,199,864 A * | 4/1980 | Ashman | 433/175 |
| 4,229,170 A | 10/1980 | Perez | |
| 4,244,689 A * | 1/1981 | Ashman | 433/175 |
| 4,252,525 A | 2/1981 | Child | |
| 4,259,072 A | 3/1981 | Hirabayashi et al. | |
| 4,281,991 A | 8/1981 | Michi et al. | |
| 4,321,042 A | 3/1982 | Scheicher | |
| 4,375,967 A | 3/1983 | Schaeffer | |
| 4,379,694 A | 4/1983 | Riess | |
| 4,381,918 A | 5/1983 | Ehmford | |
| 4,411,624 A | 10/1983 | Ogino et al. | |
| 4,431,420 A | 2/1984 | Adair | |
| 4,439,152 A | 3/1984 | Small | |
| 4,448,758 A | 5/1984 | Nagai et al. | |
| 4,475,892 A | 10/1984 | Faunce | |
| 4,478,904 A | 10/1984 | Ducheyne et al. | |
| 4,483,678 A | 11/1984 | Nishio et al. | |
| 4,492,577 A | 1/1985 | Farris et al. | |
| 4,531,915 A | 7/1985 | Tatum, Jr. | |
| 4,531,916 A | 7/1985 | Scantlebury et al. | |
| 4,536,158 A | 8/1985 | Bruins et al. | |
| 4,548,959 A | 10/1985 | Nagai et al. | |
| 4,556,534 A | 12/1985 | Burnett | |
| 4,708,652 A | 11/1987 | Fujiu et al. | |
| 4,713,006 A | 12/1987 | Hakamatsuka et al. | |
| 4,722,688 A | 2/1988 | Lonca | |
| 4,731,085 A | 3/1988 | Koch | |
| 4,737,411 A | 4/1988 | Graves, Jr. et al. | |
| 4,743,260 A | 5/1988 | Burton | |
| 4,744,757 A | 5/1988 | Adair et al. | |
| 4,744,759 A | 5/1988 | Bowen | |
| 4,820,157 A | 4/1989 | Salvo | |
| 4,842,517 A | 6/1989 | Kawahara et al. | |
| 4,871,384 A | 10/1989 | Kasuga | |
| 4,872,839 A | 10/1989 | Brajnovic | |
| 4,872,840 A | 10/1989 | Bori | |
| 4,877,400 A | 10/1989 | Holsclaw | |
| 4,880,610 A | 11/1989 | Constantz | |
| 4,906,190 A | 3/1990 | Michna | |
| 4,909,738 A | 3/1990 | Ai et al. | |
| 4,957,554 A | 9/1990 | Mathers et al. | |
| 4,957,819 A | 9/1990 | Kawahara et al. | |
| 4,960,733 A | 10/1990 | Kasuga et al. | |
| 4,969,817 A | 11/1990 | Hiranuma et al. | |
| 4,969,913 A | 11/1990 | Ojima | |
| 4,983,182 A | 1/1991 | Kijima et al. | |
| 5,000,685 A | 3/1991 | Brajnovic | |
| 5,002,488 A | 3/1991 | Homsy | |
| 5,004,421 A | 4/1991 | Lazarof | |
| 5,007,835 A | 4/1991 | Valen | |
| 5,009,709 A | 4/1991 | Ibsen et al. | |
| 5,049,074 A | 9/1991 | Otani et al. | |
| 5,055,497 A | 10/1991 | Okada et al. | |
| 5,061,285 A | 10/1991 | Koch | |
| 5,062,798 A | 11/1991 | Tsuge et al. | |
| 5,064,731 A | 11/1991 | Miyazaki et al. | |
| 5,076,789 A | 12/1991 | Tanaka | |
| 5,087,200 A | 2/1992 | Brajnovic et al. | |
| 5,120,340 A | 6/1992 | Ducheyne et al. | |
| 5,123,844 A | 6/1992 | Wakai et al. | |
| 5,125,839 A | 6/1992 | Ingber et al. | |
| 5,125,971 A | 6/1992 | Nonami et al. | |
| 5,139,424 A | 8/1992 | Yli-Urpo | |
| 5,152,687 A | 10/1992 | Amino | |
| 5,176,747 A | 1/1993 | Panzera et al. | |
| 5,180,303 A | 1/1993 | Homburg et al. | |
| 5,186,626 A | 2/1993 | Tanaka | |
| 5,192,325 A | 3/1993 | Kijima et al. | |
| 5,194,000 A | 3/1993 | Dury | |
| 5,194,001 A | 3/1993 | Salvo | |
| 5,199,873 A | 4/1993 | Schulte et al. | |
| 5,205,745 A | 4/1993 | Kamiya et al. | |
| 5,232,365 A | 8/1993 | Ikehara | |
| 5,232,878 A | 8/1993 | Kasuga et al. | |
| 5,236,458 A | 8/1993 | Ducheyne et al. | |
| 5,238,405 A | 8/1993 | Marlin | |
| 5,254,005 A | 10/1993 | Zuest | |
| 5,282,861 A * | 2/1994 | Kaplan | 623/23.51 |
| 5,282,863 A | 2/1994 | Burton | |
| 5,288,232 A | 2/1994 | Panzera et al. | |
| 5,306,673 A | 4/1994 | Hermansson et al. | |
| 5,308,391 A | 5/1994 | Komma et al. | |
| 5,310,343 A | 5/1994 | Hasegawa et al. | |
| 5,312,254 A | 5/1994 | Rosenlicht | |
| 5,314,334 A | 5/1994 | Panzera et al. | |
| 5,342,201 A | 8/1994 | Oden | |
| 5,344,318 A | 9/1994 | Wilson et al. | |
| 5,344,457 A | 9/1994 | Pilliar et al. | |
| 5,346,397 A | 9/1994 | Braiman | |
| 5,415,546 A | 5/1995 | Cox, Sr. | |
| 5,419,702 A | 5/1995 | Beaty et al. | |
| 5,425,640 A | 6/1995 | Scharf | |
| 5,439,380 A | 8/1995 | Marlin | |
| 5,443,515 A | 8/1995 | Cohen et al. | |
| 5,449,291 A | 9/1995 | Lueschen et al. | |
| 5,458,488 A | 10/1995 | Chalifoux | |
| 5,468,544 A | 11/1995 | Marcolongo et al. | |
| 5,470,230 A | 11/1995 | Daftary et al. | |
| 5,476,383 A | 12/1995 | Beaty et al. | |
| 5,549,123 A | 8/1996 | Okuyama et al. | |
| 5,554,665 A | 9/1996 | Tateosian et al. | |
| 5,562,733 A | 10/1996 | Weissbach et al. | |
| 5,571,016 A | 11/1996 | Ingber et al. | |
| 5,572,652 A | 11/1996 | Robusto et al. | |
| 5,575,652 A | 11/1996 | Gaffar et al. | |
| 5,584,693 A | 12/1996 | Nishihara | |
| 5,591,030 A | 1/1997 | Thiel et al. | |
| 5,612,049 A | 3/1997 | Li et al. | |
| 5,614,330 A | 3/1997 | Panzera et al. | |
| 5,621,035 A | 4/1997 | Lyles et al. | |
| 5,624,262 A | 4/1997 | Yarovesky et al. | |
| 5,645,934 A | 7/1997 | Marcolongo et al. | |
| 5,674,069 A | 10/1997 | Osorio | |
| 5,676,745 A | 10/1997 | Kelly et al. | |
| 5,683,249 A | 11/1997 | Ibsen et al. | |
| 5,685,714 A | 11/1997 | Beaty et al. | |
| 5,695,337 A | 12/1997 | Tyszbiat Sadoun | |
| 5,697,785 A | 12/1997 | Delahaye | |
| 5,697,976 A | 12/1997 | Chesterfield et al. | |
| 5,697,997 A | 12/1997 | Aronsson et al. | |
| 5,698,019 A | 12/1997 | Frank et al. | |
| 5,713,994 A | 2/1998 | Kramer et al. | |
| 5,723,007 A | 3/1998 | Engel et al. | |
| 5,727,943 A | 3/1998 | Beaty et al. | |
| 5,755,809 A | 5/1998 | Cohen et al. | |

(56) References Cited

U.S. PATENT DOCUMENTS

| | | |
|---|---|---|
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,951,290 A | 9/1999 | Ardizio et al. |
| 5,951,293 A | 9/1999 | Billet et al. |
| 5,951,295 A | 9/1999 | Lyles et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 * | 1/2001 | Shoher et al. ............... 623/23.6 |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,213,775 B1 | 4/2001 | Reipur |
| 6,214,368 B1 | 4/2001 | Lee et al. |
| 6,224,662 B1 | 5/2001 | Nemeth |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,202 B1 | 1/2002 | Evans et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,854,972 B1 | 2/2005 | Elian |
| 6,878,456 B2 | 4/2005 | Castro et al. |
| 6,881,488 B2 | 4/2005 | Giordano |
| 6,916,177 B2 | 7/2005 | Lin et al. |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,974,625 B2 * | 12/2005 | Hunter et al. ............. 428/304.4 |
| 6,976,999 B2 | 12/2005 | Charlebois et al. |
| 6,984,261 B2 | 1/2006 | Cummings et al. |
| 6,986,660 B2 | 1/2006 | Kumar et al. |
| 6,994,726 B2 | 2/2006 | Lin et al. |
| 7,011,522 B2 | 3/2006 | Panzera et al. |
| 7,291,012 B2 | 11/2007 | Lyren |
| 7,291,013 B2 * | 11/2007 | Aravena et al. ............. 433/173 |
| 7,648,735 B2 | 1/2010 | Hunter et al. |
| 7,708,557 B2 * | 5/2010 | Rubbert ....................... 433/173 |
| 8,071,574 B2 | 12/2011 | Bobyn et al. |
| 8,075,312 B2 | 12/2011 | Collins et al. |
| 8,113,829 B2 | 2/2012 | Sachdeva et al. |
| 8,562,346 B2 | 10/2013 | Collins et al. |
| 8,562,348 B2 * | 10/2013 | Collins et al. ............... 433/174 |
| 8,602,780 B2 * | 12/2013 | Rubbert ....................... 433/173 |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160175 A1 * | 10/2002 | Pirhonen .................... 428/297.4 |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |

(56) References Cited

U.S. PATENT DOCUMENTS

| | | |
|---|---|---|
| 2003/0096214 A1 | 5/2003 | Luthardt et al. |
| 2003/0134925 A1 | 7/2003 | Guzauskas |
| 2003/0148247 A1 | 8/2003 | Sicurelli et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0048440 A1 | 3/2005 | Feng |
| 2005/0070782 A1 | 3/2005 | Brodkin |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1* | 6/2005 | Justin .............. A61C 8/0012 427/2.26 |
| 2005/0184134 A1 | 8/2005 | Charlebois et al. |
| 2005/0191248 A1 | 9/2005 | Hunter et al. |
| 2005/0214716 A1 | 9/2005 | Weber et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2006/0105295 A1 | 5/2006 | Mayer et al. |
| 2007/0015110 A1 | 1/2007 | Zhang et al. |
| 2007/0111165 A1 | 5/2007 | Wallick et al. |
| 2007/0118221 A1 | 5/2007 | Robie et al. |
| 2007/0148621 A1 | 6/2007 | Yakir |
| 2007/0184265 A1 | 8/2007 | Ranganathan et al. |
| 2007/0269769 A1* | 11/2007 | Marchesi .............. 433/215 |
| 2008/0050699 A1 | 2/2008 | Zhang et al. |
| 2008/0090208 A1* | 4/2008 | Rubbert .............. A61C 13/0004 433/173 |
| 2008/0241793 A1* | 10/2008 | Collins et al. .............. 433/174 |
| 2008/0300716 A1 | 12/2008 | Kopelman et al. |
| 2008/0305458 A1 | 12/2008 | Lemchen |
| 2009/0011384 A1 | 1/2009 | Collins et al. |
| 2009/0036908 A1 | 2/2009 | Zokol et al. |
| 2009/0042167 A1* | 2/2009 | Van Der Zel .............. 433/215 |
| 2009/0061387 A1* | 3/2009 | Lomicka et al. .............. 433/173 |
| 2009/0061388 A1* | 3/2009 | Collins et al. .............. 433/174 |
| 2009/0061389 A1 | 3/2009 | Lomicka et al. |
| 2009/0098510 A1 | 4/2009 | Zhang |
| 2009/0098511 A1* | 4/2009 | Zhang .............. 433/201.1 |
| 2009/0215007 A1* | 8/2009 | Caterini .............. A61L 27/047 433/173 |
| 2010/0003638 A1* | 1/2010 | Collins .............. A61C 8/0012 433/174 |
| 2010/0003639 A1 | 1/2010 | Salvi et al. |
| 2010/0003640 A1 | 1/2010 | Damstra et al. |
| 2010/0114314 A1 | 5/2010 | Lomicka et al. |
| 2010/0323324 A1* | 12/2010 | Kim .............. 433/173 |
| 2012/0064489 A1* | 3/2012 | Rubbert et al. .............. 433/175 |
| 2012/0251980 A1 | 10/2012 | Bassett et al. |
| 2013/0344457 A1 | 12/2013 | Collins et al. |
| 2013/0344459 A1 | 12/2013 | Collins et al. |
| 2014/0017633 A1 | 1/2014 | Lomicka |
| 2014/0023992 A1 | 1/2014 | Willis et al. |
| 2014/0030675 A1 | 1/2014 | Sanchez et al. |
| 2014/0038132 A1 | 2/2014 | Willis et al. |

FOREIGN PATENT DOCUMENTS

| | | |
|---|---|---|
| DE | 19529036 | 3/1997 |
| DE | 10105398 | 8/2002 |
| EP | 0266313 | 5/1988 |
| EP | 0271236 | 6/1988 |
| EP | 0345581 | 12/1989 |
| EP | 0366018 | 2/1990 |
| EP | 0417018 | 3/1991 |
| EP | 0467948 | 1/1992 |
| EP | 0498923 | 8/1992 |
| EP | 0333503 | 2/1993 |
| EP | 0560279 | 9/1993 |
| EP | 0806211 | 11/1997 |
| EP | 0950421 | 10/1999 |
| EP | 1281372 | 2/2003 |
| EP | 1598028 | 11/2005 |
| EP | 1712205 | 10/2006 |
| FR | 2796265 | 1/2001 |
| GB | 1526780 | 9/1978 |
| GB | 2401867 | 11/2004 |
| GB | 2416996 | 2/2006 |
| JP | 61275205 | 12/1986 |
| JP | 1025849 | 1/1989 |
| JP | 63290559 | 11/1998 |
| JP | 2002126071 | 5/2002 |
| WO | 8900410 | 1/1989 |
| WO | 9011979 | 11/1990 |
| WO | 9320773 | 10/1993 |
| WO | 9421190 | 9/1994 |
| WO | 9528973 | 11/1995 |
| WO | 9721393 | 6/1997 |
| WO | 9741809 | 11/1997 |
| WO | 9830170 | 7/1998 |
| WO | 0021455 | 4/2000 |
| WO | 0132072 | 5/2001 |
| WO | 0187193 | 11/2001 |
| WO | 0234155 | 5/2002 |
| WO | 0236039 | 5/2002 |
| WO | 02062901 | 8/2002 |
| WO | 02064100 | 8/2002 |
| WO | 03065939 | 8/2003 |
| WO | 03065996 | 8/2003 |
| WO | 03078508 | 9/2003 |
| WO | 03094774 | 11/2003 |
| WO | 2004054464 | 7/2004 |
| WO | 2007027794 | 3/2007 |
| WO | WO 2009154560 A1 * | 12/2009 |

OTHER PUBLICATIONS

Computer-Guided Immediate Provisionalization of Anterior Multiple Adjacent Implants: Surgical and Prosthodontic Rationale, Joseph Y. K. Kan, Practical Procedures & Aethetic Dentistry, vol. 18, No. 10, 617-623, 2006.

Flocculants, Binders, and Bonds, Chapter 11, Molecular Binders pp. 173-177, 1995.

Injection Molding, Chapter 24, Equipment and Material Variables in Injection Molding, pp. 479-481.

Innovative Ceramic-Fiber Technology Energizes Advanced Cerametrics, Richard B. Cass et al. Story—the American Ceramic Society, American Ceramics Society Bulletin, Nov. 2003, pp. 9701-9706.

Peek-Classix, Information Sheet Invibio Ltd., Properties of Peek-Classix White Granular, Nov. 2003.

Presurgical Planning With CT-Derived Fabrication of Surgical Guides, Scott D. Ganz, J Oral Maxillofac Surg 63:59-73, 2005, Suppl 2.

Prosthetically Directed Implant Placement ing Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.

Shape Optimization of Randomly Oriented Short Fibers for Bone Cement Reinforcements, Yan Zhou, Chaodi Li, James J. Mason, Materials Science & Engineering A 393 (2005) 374-381.

(56) References Cited

OTHER PUBLICATIONS

The Clinical Assessment of a Ceramic-Coated Transmucosal Dental Implant Collar; International Journal of Prosthodonics; 1996—vol. 9, Issue 5; pp. 466-472.
Two Applications of Transmucosal Milled Ceramic in Implantology; Preliminary Clinical Examples; Implant Quintessence Dentistry International; Aug. 1996—vol. 27, Issue 8, pp. 533-547.
International Search Report from related application PCT/2006/033893, dated Jan. 29, 2007, 1 page.
International Search Report from related application PCT/2006/020130, dated Feb. 6, 2007, 10 pages.
International Search Report from related application PCT/2007/069562, dated Jul. 7, 2008, 1 page.
International Search Report from related application PCT/2008/074616; dated Dec. 16, 2008; 4 pages.
International Search Report from related application PCT/2008/074645, dated Dec. 29, 2008; 9 pages.
International Search Report from related application PCT/2008/074642; dated Feb. 12, 2009, 4 pages.
International Search Report from related application PCT/2008/074655; dated Feb. 18, 2009, 9 pages.
International Search Report from related application PCT/US2009/048469; dated Oct. 19, 2009, 9 pages.
International Search Report from related application PCT/2009/048476; dated Dec. 10, 2009; 13 pages.
International Search Report from related application PCT/2009/048481; dated Dec. 10, 2009; 13 pages.
International Search Report from related application PCT/2009/062308; dated Jan. 21, 2010; 17 pages.
International Search Report from related application PCT/2009/048456; dated Apr. 27, 2010; 5 pages.
"U.S. Appl. No. 13/408,002, Non Final Office Action mailed Jul. 2, 2013", 9 pgs.
"U.S. Appl. No. 13/408,002, Preliminary Amendment filed Feb. 29, 2012", 6 pgs.
"U.S. Appl. No. 13/408,002, Response filed May 14, 2013 to Restriction Requirement mailed Apr. 15, 2013", 9 pgs.
"U.S. Appl. No. 13/408,002, Restriction Requirement mailed Apr. 15, 2013", 6 pgs.
"European Application Serial No. 10007155.4, Examination Notification Art. 94(3) mailed Jun. 13, 2013", 4 pgs.
"European Application Serial No. 10007155.4, Office Action mailed Oct. 31, 2011", 2 pgs.
"European Application Serial No. 10007155.4, Response filed Oct. 23, 2013 to Examination Notification Art. 94(3) mailed Jun. 13, 2013", 6 pgs.
"U.S. Appl. No. 13/408,002, Final Office Action mailed Feb. 14, 2014", 9 pgs.
"U.S. Appl. No. 13/408,002, Response filed Dec. 31, 2013 to Non-Final Office action mailed Jul. 2, 2013", 11 pgs.
"European Application Serial No. 10007155.4, Examination Notification Art. 94(3) mailed May 13, 2015", 5 pgs.
U.S. Appl. No. 13/408,002, filed Feb. 29, 2012, Method of Forming Patient Specific Implants With Improved Osseointegration.

* cited by examiner

PATIENT-SPECIFIC IMPLANTS WITH IMPROVED OSSEOINTEGRATION

FIELD OF THE INVENTION

The present application is directed to endosseous implants and, more particularly to implants customized for specific patients and that have features for improved integration with surrounding bone.

BACKGROUND OF THE INVENTION

One form of implant is the root-form dental implant which is placed in extraction site cavities or drilled holes in the mandible or maxillae to support one or more tooth-shaped prosthesis. The root-form implant generally has a cylindrical outer surface to engage bone. While such dental implants may be provided in a limited number of different lengths and diameters, these sizes may not match the exact size needed to sufficiently fill an extraction site to provide prosthesis with proper structural support and proper aesthetic appearance. This is particularly true if the extraction site is an irregular shape or is in an area where there is a ridge defect.

Another form of dental implant is the plate-form or blade-form implant which has a flat plate as the anchor to be placed in the mandible or maxillae, and typically has posts to support one or more prosthetic teeth or crowns either individually or structurally interconnected by a bridge. A plate-form implant may be more stable than a root-form implant in areas where multiple teeth are missing, facial-lingual bone width is small and/or alveolar ridge height is limited. The location of the posts on the implant, however, is preset and may not correspond with the optimal location of the crowns (or bridge) on the jaw. Special allowances then need to be made in the crowns or bridge to account for this which may result in aesthetic compromises. Also, the flat area of the plate faces facially and lingually and is manually bent at the time of surgery to conform to the curvature of the jaw. This procedure is inexact and may damage the implant. A non-fitting curvature of the plate may also cause gaps between the plate and adjacent bone that could compromise healing or may require further time consuming shaping of the bone.

Furthermore, the blade-form implant has been known to promote fibro-osseous integration as opposed to osseointegration. Osseointegration is defined as a direct connection between the implant and viable bone that results in a very immobile implant. In fibrous integration, the implant is surrounded by a membrane like layer of less mineralized tissue that does not hold the implant as well as bone tissue. While fibrous tissue connection may be beneficial because it stimulates the periodontal ligament which cushions the implant from occlusal loads, some degree of osseointegration must occur to provide adequate support to the implant. A total fibrous encapsulation of the implant isolates the implant mechanically from the viable bone of the jaw and endangers the long term survival of the implant.

Yet another form of implant is a bone graft. Sometimes it may be necessary to perform some type of a bone restoring process before a tooth implant can be placed. For instance, if the patient has poor dental health and the patient has been wearing non-implant supported dentures for many years, defects or holes may exist in the bone. The best treatment option in such cases is to repair the bone defects. Larger bone defects are currently treated by harvesting the patients own bone or by using specially treated cadaver bone. The bone harvesting surgery, however, can be more invasive then the bone grafting surgery and adds to the patients discomfort and healing time. Also, whether harvested or cadaver bone is used, the surgeon must shape these bone pieces by hand at the time of surgery to fit the defect. Hand shaping is not exact and gaps between the graft and defect (i.e., bone surface) may compromise healing. Finally, even if an implant customization process could be used, it would be difficult to pre-shape natural bone using automated machining processes without damaging the bone.

Thus, an endosseous implant made of a material that is easily shaped yet provides strong and rapid osseointegration is desired.

DETAILED DESCRIPTION OF THE PREFERRED EMBODIMENTS

The solution to the problems mentioned above is an endosseous implant with a porous material that integrates strongly with bone and may be easily shaped to match the dimensions of a specific patient. In one form, the porous material is useful as a bone substitute and/or cell and tissue receptive material. An example of such a material is produced using Trabecular Metal® technology generally available from Zimmer, Inc., of Warsaw, Ind. Trabecular Metal® is a trademark of Zimmer Technology, Inc. Such a material may be formed from a foamed polymer (such as polyurethane, as one example) that is reduced to a reticulated vitreous carbon foam substrate or skeleton. The carbon skeleton is infiltrated and coated with a first layer of biocompatible metal, such as tantalum, to produce a low density material, and then plated with a second layer of tantalum to produce a high density material. The metal is plated on the carbon substrate by a chemical vapor deposition (CVD) process in the manner disclosed in detail in U.S. Pat. No. 5,282,861, the disclosure of which is fully incorporated herein by reference. Other metals such as niobium, or alloys of tantalum and niobium alone, with one another, or with other metals may also be used.

Figure 1:
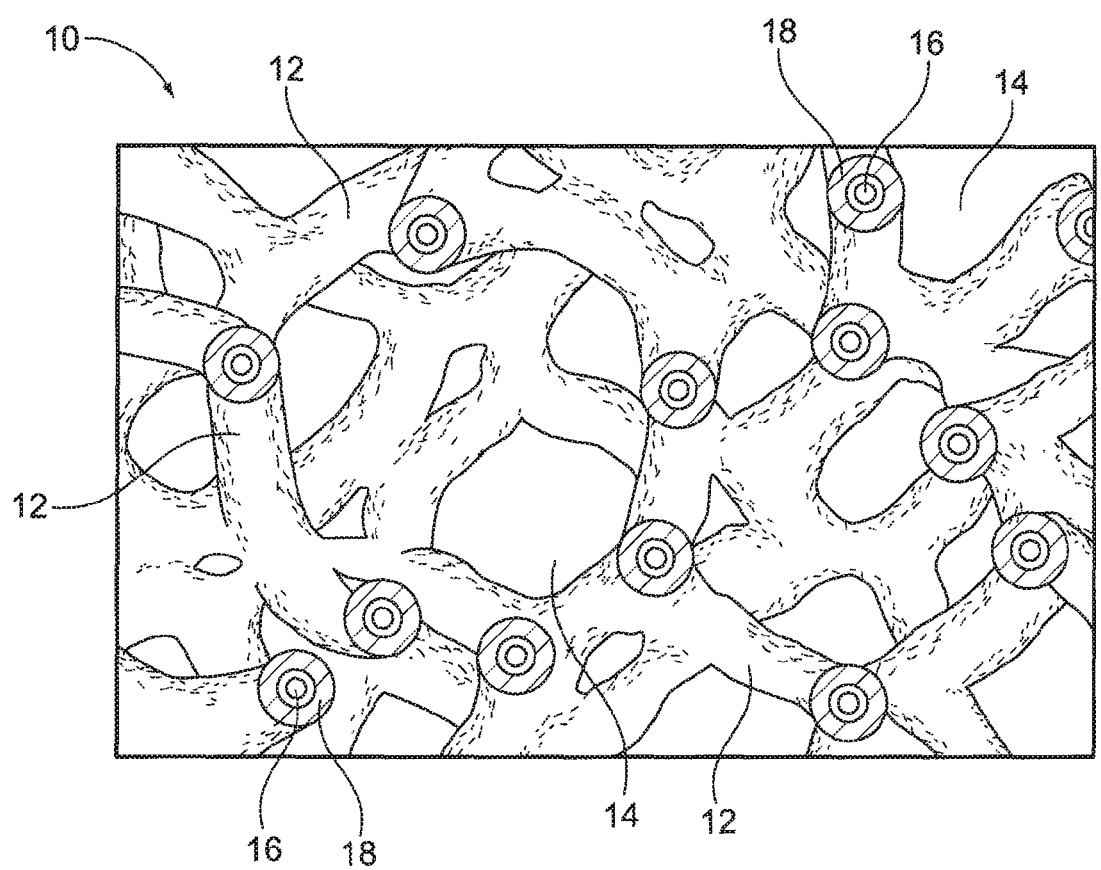
FIG. 1 is an enlarged fragmentary view of a porous metal portion for any of the embodiments herein and in accordance with one aspect of the present invention.

Referring to FIG. 1, an example of the porous metal structure 10 includes a large plurality of ligaments 12 defining open spaces 14 therebetween, with each ligament 12 generally including a carbon core 16 covered by a thin film of metal 18 such as tantalum, for example. The open spaces 14 between ligaments 12 form a matrix of continuous channels having no dead ends, such that growth of cancellous bone through porous metal structure 10 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor an implant into the surrounding bone of a patients jaw which increases stability (herein, jaw generally refers to both the mandible and maxillae).

The rough exterior surface of such porous metal portion has a relatively high friction coefficient with adjacent bone forming the bore or cavity that receives the implant to further increase initial stability. Thus, this structure can produce superior aesthetic results by restricting movement of the implant. These implants can be placed without supplementary surgical procedures, such as bone grafting, and can be placed in areas where traditional implants have been less successful, such as with reduced or decayed alveolar sections.

More specifically, for implants that are press-fit into a bore or cavity in bone, the high level of friction between the porous material and the bone provides immediate stability post surgery. The tantalum struts that extend from the surface of the material create a rasping action that may stimulate bone growth and anchor the implant at the time of placement. The extremely biocompatible tantalum metal that the porous material is made from allows bone to directly oppose the material. The tantalum forms a porous scaffolding that allows bone to grow into the material providing a rapid osseointegration response that quickly augments the initial mechanical fixation to secure the implant. The implant with in-grown bone may have stability greater than a comparably sized implant with only on-grown bone. Finally, the composite of in-grown bone and such a porous material has elastic properties much closer to bone than a solid metal implant, creating a loading environment that is conducive to maintaining bone near the implant.

Regarding the initial stability, as an implant with the porous material is inserted into the bore or cavity in bone, the porous material will bite into the bone by grating, chipping and/or flaking bone pieces off of the bone sidewalls against which the implant device is being placed. When the implant is press-fit into the bore or cavity, this "rasping" action may form slight recesses or indents within the sidewall. This restricts rotational or twisting motion of the implant device within the bore or cavity since the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. Thus, the porous material has increased resistance to twisting or rotation, allows for immediate or very early loading, and increases long-term stability due to the improved osseointegration. Such an implant with ingrown bone has stability greater than a comparably sized implant with only on-grown bone. These advantages may be realized no matter the form of the porous implant (e.g., root-form, plate-form, or a larger implant block as described in detail below).

Porous structure 10 may be made in a variety of densities in order to selectively tailor the structure for particular applications. In particular, the porous tantalum may be fabricated to virtually any desired porosity and pore size, whether uniform or varying, and can thus be matched with the surrounding natural bone in order to provide an improved matrix for bone in-growth and mineralization. This includes a gradation of pore size on a single implant such that pores are larger on an apical end to match cancellous bone and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all or some of the pores with a solid material as follows.

The porous structure may be infiltrated at least partially with solid filler material such as a non-resorbable polymer or a resorbable polymer to provide additional initial mechanical strength and stability in high arcs of mechanical stress. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethyl methacrylate (PMMA), polyetherimide, polysulfone, and polyphenolsulfone. Examples of resorbable polymers may include poly lactic acid (PLA), poly glycolic acid (PGA), poly lactic co-glycolic acid (PLGA), polyhydroxybutyrate (PHB), polyhydroxyvalerate (PHV), and copolymers thereof, polycaprolactone, polyanhydrides, and polyorthoesters. The resorbable material would resorb as the bone grows in and replaces it, which maintains the strength and stability of the implant.

Figure 14:
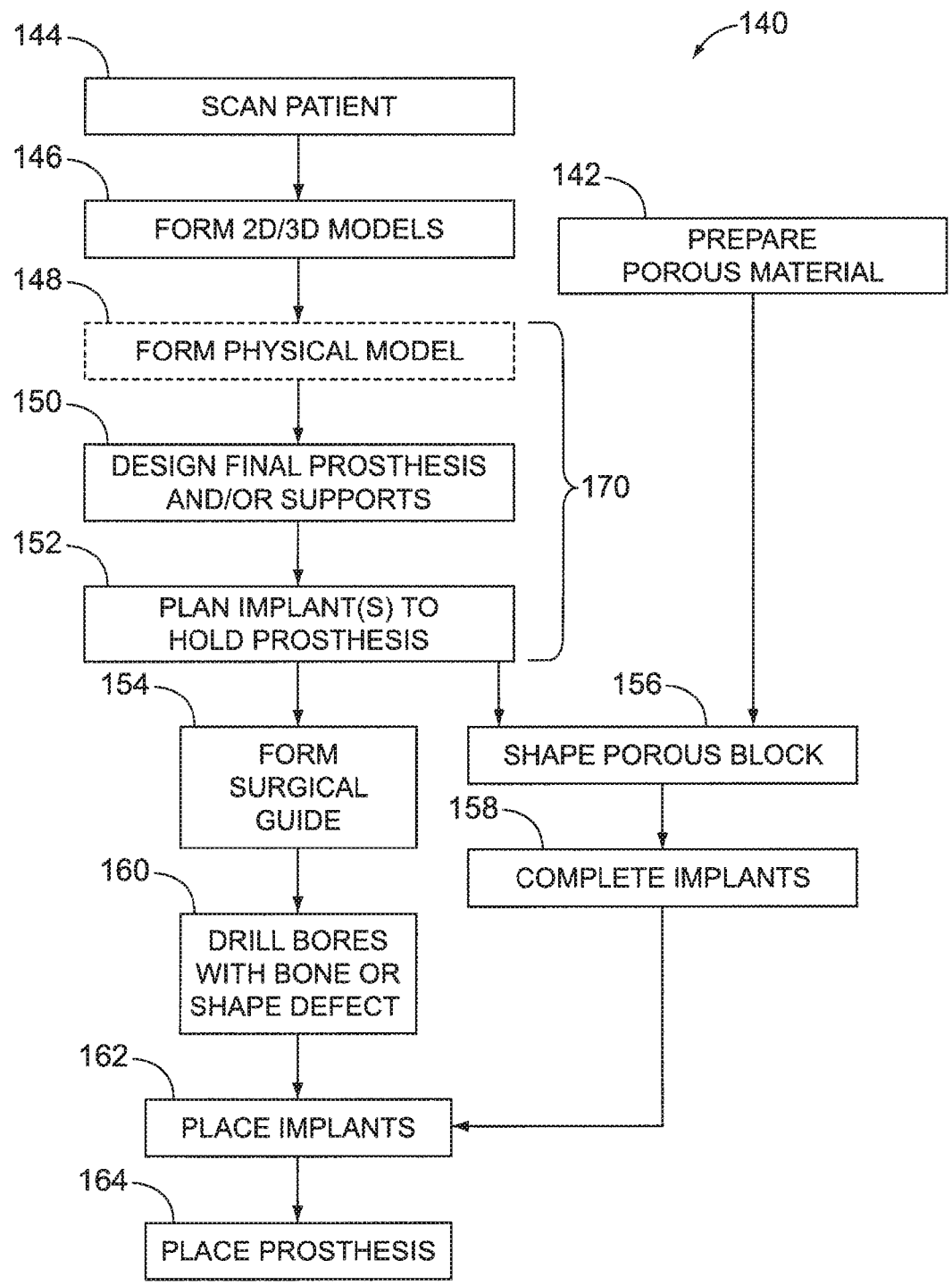
FIG. 14 is a flow chart showing a simplified process for forming an implant in accordance with the present invention.

Referring to FIG. 14, a process 140 is provided to use the porous material 10 which is fabricated in the process described above (and indicated as 142 on FIG. 14) for a variety of patent-specific, porous bone implants. These implants are created by using imaging technologies that allow either radiographic or visible light scan of the human body, such as the jaw and dentition, that can be combined with computer aided design and computer aided manufacturing (CAD, CAM), and rapid prototyping technologies to make patient-specific dental products.

First, a computerized axial tomography (CAT) scan is taken 144 of the area of the patient's body to receive the implant in order to obtain the patient's dimensions and particularly the dimensions of the defect or cavity to be filled by the implant. While the example of a dental implant or jaw implant is used below, it will be understood that the bone implants may be formed for many other bones in the body. In the present example, to obtain the dimensions of the patient, a CAT scan of the patient's head is taken including the defect and adjacent dentition. This may require the patient to wear scanning appliances during the scan. Such appliances may have markers or pins that are detected by the scanner to indicate the location and shape of important dentition such as the position of each tooth. For dental applications, the patient is typically scanned using cone beam CAT technology.

The CAT scan outputs data in a format known as Diacom data. Each voxel or 3D element (pixel) is recorded in the Diacom file with 3D position data and radio-opacity data. A process known as segmentation is used to create separate 3D rendering of each tissue type based on the degree of radio-opacity. The resulting rendering separates areas of hard and soft tissue by portraying the tissue as different colors on the computer screen and/or by filtering the tissue types by layers that can be selected on or off in a computer program. With this technology, the captured data includes information on structure underlying outer bone surfaces to be avoided such as nerve location, sinus cavities, and tooth roots. This information also may include bone density which is important for further determining the size, shape, and location of the implant.

Alternatively, an impression taking technique utilizing an alginate, silicone, polyvinyl siloxane, polyether, zinc oxide eugenol paste or other impression material typically used in dentistry could be used to capture the shape of the bony defect. The impression material would be injected into a mold around the defect and then removed to form a negative of the defect. The impression might also be used to capture the form and location of adjacent detention to establish "reference" geometry to locate the defect. A visible light scanner can then be used on the model to create the digital data to form the 2D or 3D computer representation of patient anatomy.

Optionally, a visible light scanner may be used to scan directly in the mouth, skipping the impression taking step. These intra-oral scanners create the digital data directly from a scan of patient anatomy.

Visible light scans can be used to create point cloud, STL or IGES data formats that are readily used by computer software to create 2D or 3D models similar to the models created from the Diacom data from the CAT scan. These models lack the bone density data but have an advantage because visible light scans do not suffer from the starburst or scatter effect created when x-ray interact with metal fillings in the teeth. It is possible to combine CAT scan and visible light data to create a composite digital images of both the dentition and the bone.

Software then uses the scan data and mathematical algorithms to create and display 146 a 2D and 3D representation of patient anatomy and the area to be repaired. Software capable of portraying the 2D and 3D renderings include, for example, Simplant by Materialize, Co-Diagnostic by IVS and si-CAT by Sirona. Any of these, or custom software, could render the non-edentulous area or defect in the face or jaw that is to be restored. Optionally, once the virtual existing structure is established, an actual physical model may be produced 148 if it is deemed helpful to locate existing dentition, shape the final prosthesis, and/or to help with surgical planning. This may be performed by rapid prototyping technology. Alternatively, or additionally, a stone model developed from impressions of the implant may be used in conjunction with the virtual models.

After the non-edentulous area or defect, and surrounding bone, are properly dimensioned on the models, the programs may be used to build virtual structures inside of the rendered 2D or 3D environment. Building virtual structures using the rendered anatomical data as a reference is similar to CAD systems that use parametric modeling capabilities. Examples of such CAD systems are Unigraphics or Solidworks. Pointing devices such as trackballs or mice are used to "pick" elements on the rendered patient anatomy and then extend from these elements flat and curved surfaces that are then sewn together into a solid.

One planning strategy that may be used in the dental field is to first design 150 the final tooth shape prosthesis and/or any support posts or abutments on the virtual model, and then size, shape, and locate 152 the implant or implants on the virtual model, needed to support those prosthesis. The virtual teeth also can be used to assess proper bite and chewing function. Rapid prototyping may then be used to form a coping to build a final prosthesis, and the posts may be formed by machining as described below. Once the implant or 3D volume is formed in the model, it can be isolated for fabrication.

Figure 15:
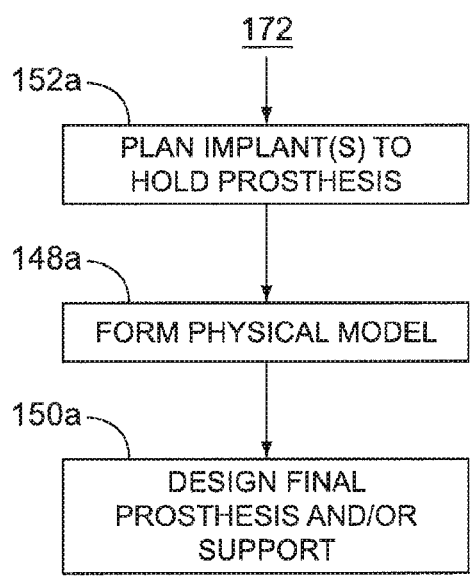
FIG. 15 is a flow chart showing alternative steps for the process of FIG. 14.

Referring to FIG. 15, in an alternative procedure 172, the implant is designed 152*a* on the 3D model, and then a physical model of the jaw with the implant is produced 148*a* from the 3D model. The abutments and final prosthesis are then formed 150*a* on the physical model.

Figure 16:
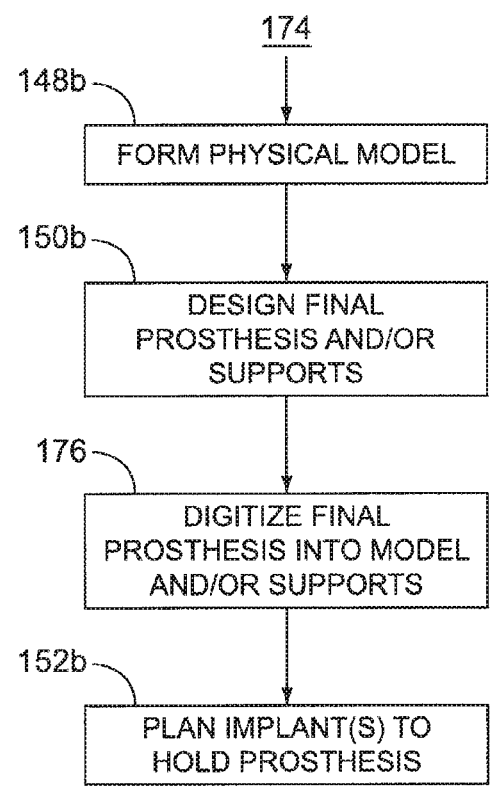
FIG. 16 is a flow chart showing further alternative steps for the process of FIG. 14.

Referring to FIG. 16, in yet another alternative procedure 174, the abutment, posts, and or final prosthesis are formed 150*b* on a physical model made 148*b* from impressions and/or the 3D virtual model. The pieces are then scanned and digitized 176 to place them on the 3D model. Once the supports and virtual teeth are properly sized and located on the 3D model, the porous implant is designed 152*b*.

Regardless of which procedure is used, once the 3D representation of the porous block or implant is formed, the mathematical representations of the surface and 3D volumes are easily transferred from 3D modeling programs to a Computer Assisted Manufacturing (CAM) program. CAM programs trace machine paths over the imported 3D model that will eventually guide any number of types of machines during the fabrication process. The output of these programs is computer numerical control (CNC) code that can be processed by the electronic controls of fabrication equipment.

To shape 156 a block of porous material, any of the precursor stages of the porous material can be shaped before the metal layers are deposited by traditional machining operation driven by (CAD/CAM) technology. Alternatively, the 3D volume data may be used to form a mold, and the foam is initially created in the mold so that the foam is already in a near-net shape (i.e., near the final implant shape). It may also be possible to shape the foamed polymer with desired dimensions by using rapid prototype processes such as 3D printing or selective laser sintering.

As another alternative, the carbon or polymer foam can be shaped by CNC milling equipment such as that made by HAAS Automation, Inc. This may occur either before or after the first coating of metal is deposited on the foam. This near-net shaped carbon foam is then plated or replated with tantalum to create the porous implant.

Alternatively, a high density body of the foam already plated with both layers of the metal could then be cut to the designed dimensions using CNC controlled EDM (Electrical Discharge Machining). In this case, the porous material may be provided as a cube, rectangular prism, or cylinder that is shaped by the EDM process. The EDM process avoids the tendency to close pores on the surface of the porous material as occurs with other more traditional machining and milling.

In one form, after the porous block is shaped as described above, it is ready to be implanted. This type of implant may be used on the jaw when the implant will not directly support teeth for example. This may occur if the implant is used to build up bone loss or bone defect areas spaced away from the alveolar such as when dentures, bridges, or other appliances that do not require drilling into the implant are to be placed over the area of the jaw with the implant. It will be appreciated that the implant may be sufficient for bones other than the jaw.

In an alternative form, after the porous block is shaped, other parts of the implant such as support posts and prosthesis are fixed 158 to the porous block to complete the implant. The CAM software can add holes to the porous block model if needed to hold the underlying structures or post that hold the prosthetic teeth. The CAM software also produces CNC data of both the porous block with holes and the tooth supporting structures.

It will be understood that any of the posts in any of the embodiments described herein can be made of the porous metal structure 10, such as Trabecular Metal®. In this case, the block may be a single piece shaped with integral posts. Alternatively, the porous metal posts may be formed separately and subsequently attached to the block.

It also will be understood that any of the posts in any of the embodiments described herein, whether or not made of porous material, may be partially embedded in the porous block during or after the shaping of the porous block such that the implant is provided as a single, unitary component.

In one form, the tooth supporting structures or posts are made of a solid, strong metal such as titanium that is biocompatible. CNC machine tools may be used to fabricate these metal parts. Diffusion bonding, CVD bonding, and the like may be used to bond the porous metal and titanium elements. It will be understood, however, that other materials such as metals, ceramics, and composites, or porous materials as mentioned above, may be used to form the posts instead. In this way, the entire implant structure of defect filling porous block and tooth support is fabricated as a single piece for implantation.

Once the implant and any required posts and prosthesis are complete, a surgical guide may be formed 154 as described below, and the appropriate bores or shaping of the defect or extraction site may be performed 160 to receive the implant. The implant and prosthesis are then implanted 162 and 164.

Figure 2:
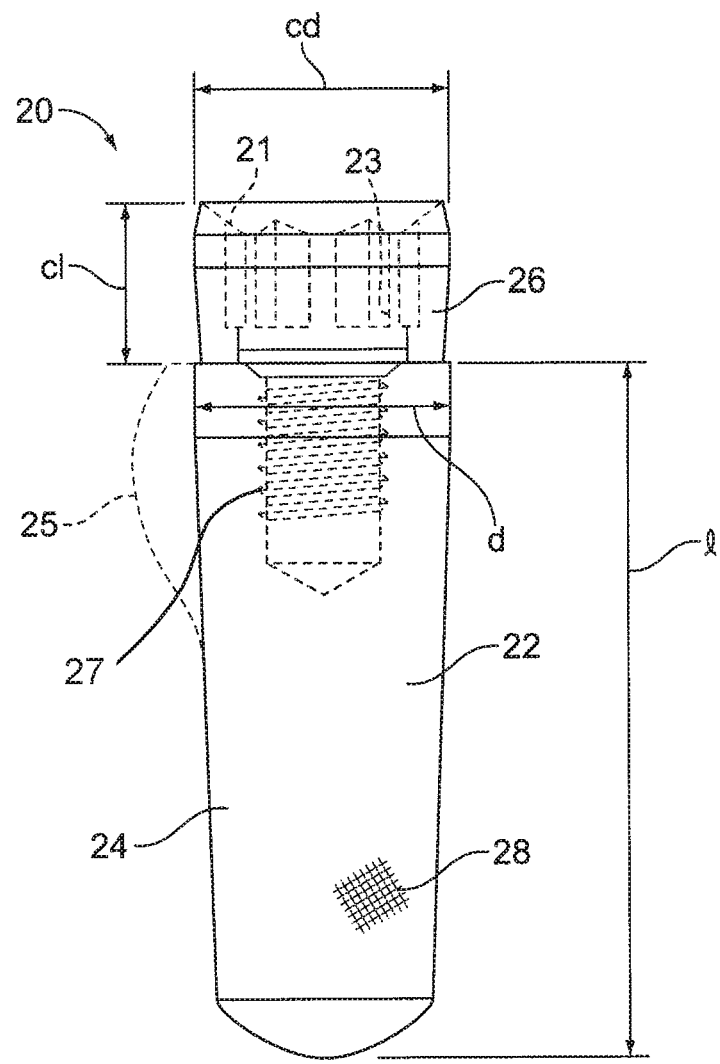
FIG. 2 is a side view of a two-stage, root-form dental implant according to one aspect of the present invention.

Referring to FIG. 2, using the methods described above, the porous material may be shaped to form a number of different patient-specific dental and maxillofacial implants that provide excellent integration with surrounding bone. In one example form, a root-form, two-stage, dental implant 20 is provided to be press-fit or threaded into a bore in the alveolar ridge to support a prosthetic tooth. Implant 20 may be fabricated using the patient-specific design and manufacturing process described above. Parameters such as the implant length, taper angles, and diameter anywhere along the taper can be specifically selected for the individual patient's anatomy. Further the exact location of the porous material of the implant and other surface roughening can be specifically selected. The prosthetic section can also be specifically designed to optimally accommodate the prosthetic tooth.

The implant 20 has a body 22 with an apical or anchor portion 24 and a collar portion 26. Collar portion 26 can be attached to anchor portion 24 at threaded interface 27. The apical portion 24 has a diameter (d) and body length (l), while the collar portion 26 has a diameter (cd) and collar height (ch) that were all set or customized according to the real dimensions of the bore or extraction site on the patient. In this example, the porous metal material 28 extends through-out the entire apical portion 24. It will be appreciated, however, that the porous material may extend only on parts of the apical portion 24 (e.g., upper, lower, inner, or outer portions). Likewise, the porous material may or may not extend on all or part of the collar portion 26. In one form, implant 20 may have a prosthetic interface 21, such as the Zimmer Dental, Inc. friction fit hexagon, within a coronal cavity 23 (shown in dash line) and accessible on the collar portion 16 to assemble and attach an abutment to the implant 20. It will be understood that while the root-form implant typically has a generally cylindrical outer surface, in the case of patient-specific implants here, the implant 20 may have an irregular shape 25 (shown in dash line) to properly fit a particular extraction site. It will be appreciated that the shape is limited only by practicality and structure on the bone to be avoided (e.g., nerves, blood vessels, etc.).

Figure 3:
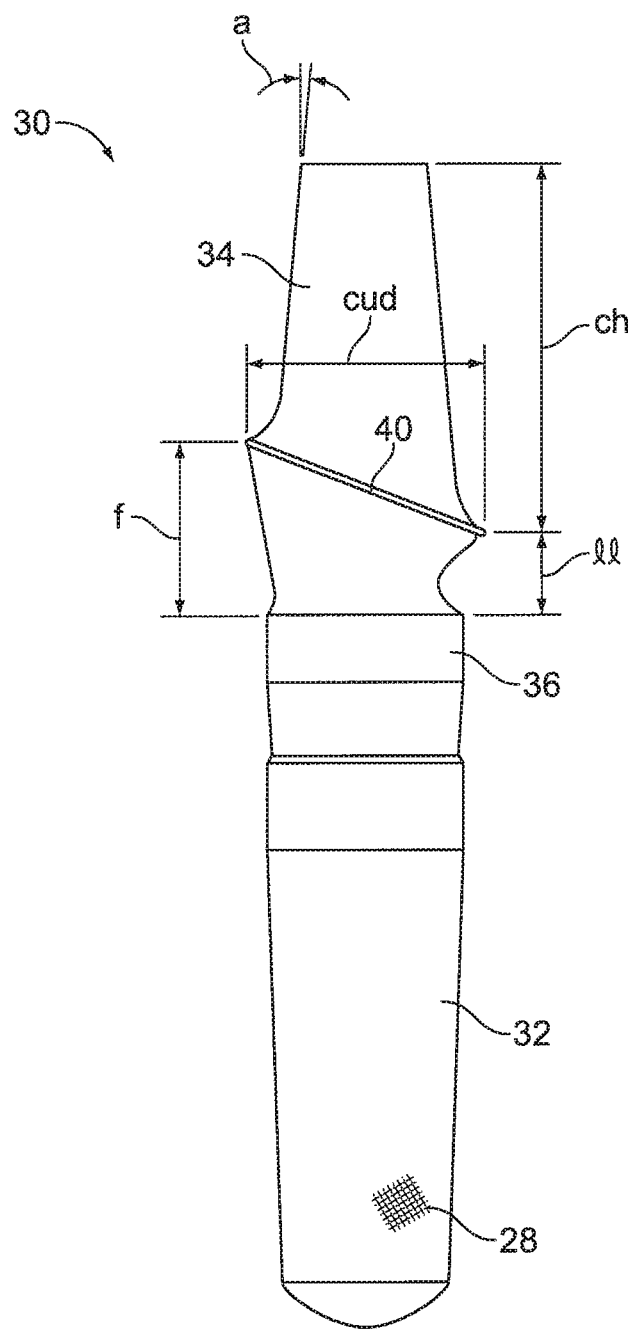
FIG. 3 is a lateral view of a one-piece, root-form dental implant according to another aspect of the present invention.
Figure 4:
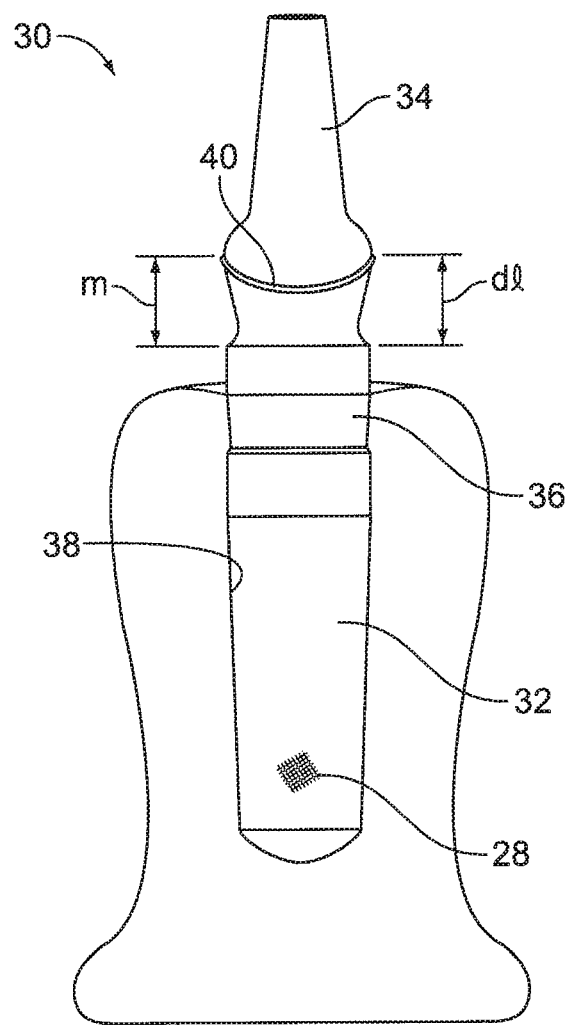
FIG. 4 is a lingual view of the one-piece dental implant of FIG. 3 shown implanted in a jaw bone.

Referring to FIGS. 3-4, a one-piece, root-form, dental implant 30 has an integrally formed anchor portion 32, abutment portion 34, and collar portion 36. In addition to the dimensions customized on the two-stage implant 20, here the one-piece implant 30 has additional dimensions that are set depending on the dimensions of the patients bone and soft tissue. For example, the implant 30 can be further customized by selecting features such as the facial (f), lingual (ll), mesial (m) and distal (dl) heights of the margin or cuff 40 to correspond to the actual height of the patient's soft tissue. Similarly, the cuff diameter (cud), the cone height (ch) and angulation (a) may be customized to correspond to the size and orientation of the prosthetic tooth to be supported.

If a non-viable natural tooth is removed though an atraumatic extraction, it is possible to place an implant very near the time of extraction with little modification to the extraction site. Using many of the imaging technologies discussed above, it is possible to digitize the shape of the extraction socket. The implant 30 is shown after being press-fit into extraction socket 38. In this case, the anchor portion 32 and the collar 34 may have an irregular shape to match the shape of the extraction socket 38 as with the implant 20. The high friction between the porous metal material of the anchor portion 32 and adjacent bone holds the implant 30 in place during healing.

Figure 5:
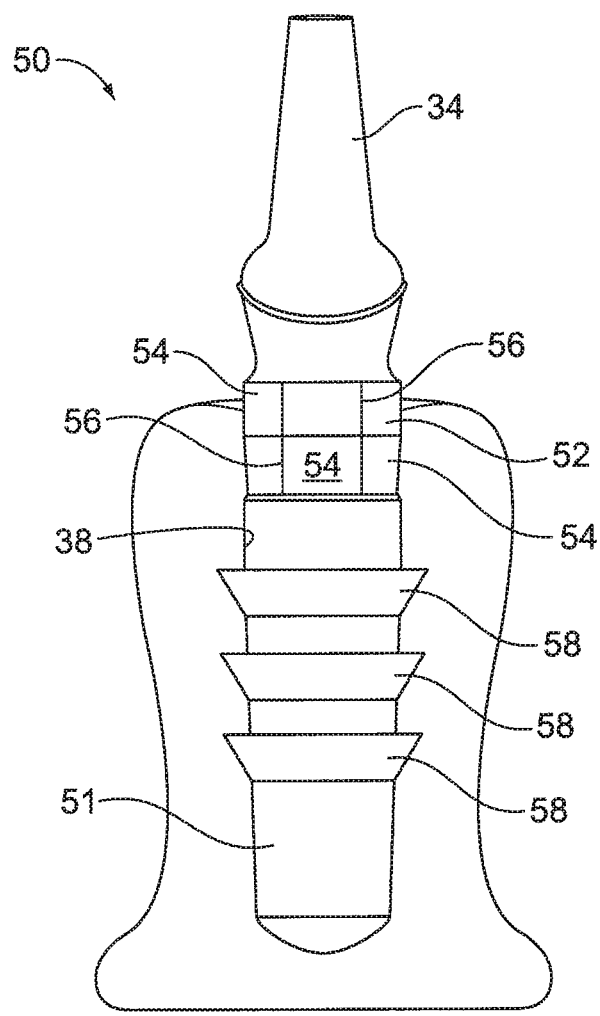
FIG. 5 is a lingual view of an alternative one-piece dental implant according to an aspect of the present invention and shown implanted in a jaw bone.

Referring to FIG. 5, an implant 50 is provided that is similar to implant 30 except that here a collar portion 52 of the implant 50 has outer surfaces 54 that meet at corners or joints 56 (e.g., polygonal) while teeth or barbs 58 are provided on an anchor portion 51 of the implant 52 to increase retention strength of the implant within the extraction site. In one form, the barbs 58 are annular and have a pointed edge pointing coronally.

Figure 6:
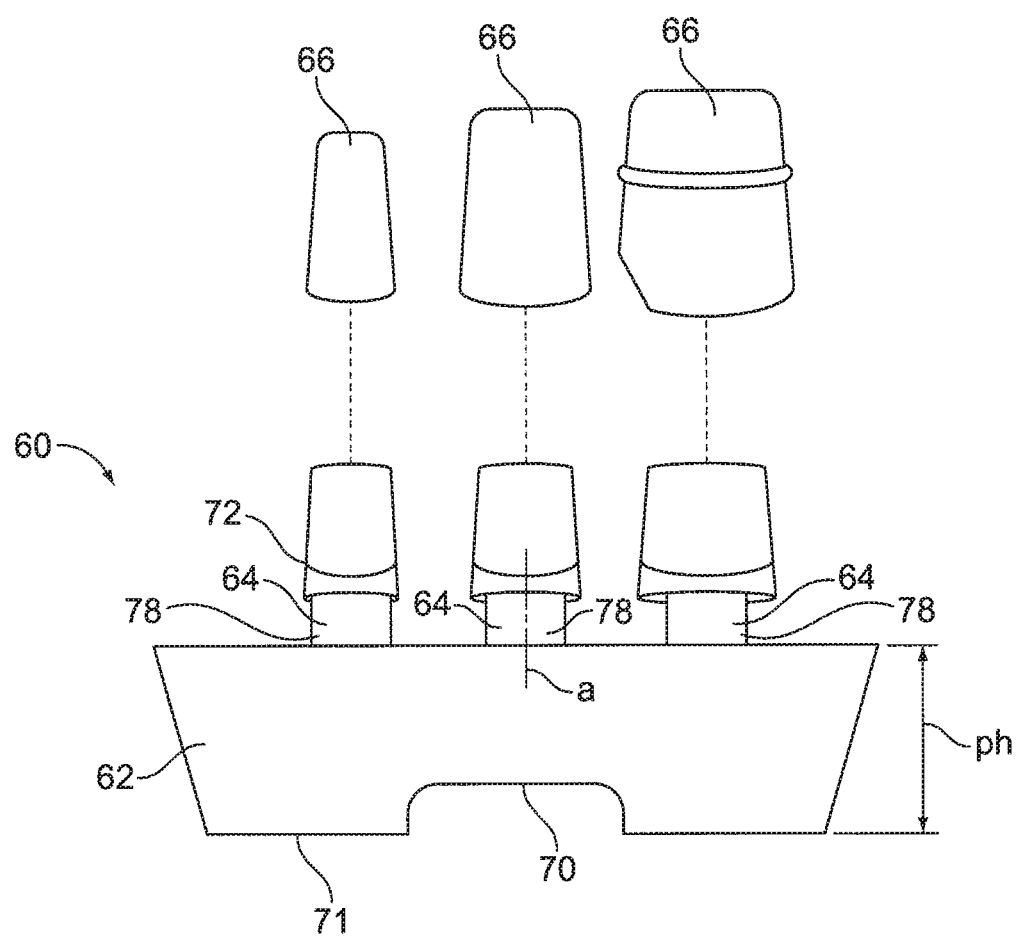
FIG. 6 is a lingual view of a plate-form dental implant according to another aspect of the present invention.
Figure 7:
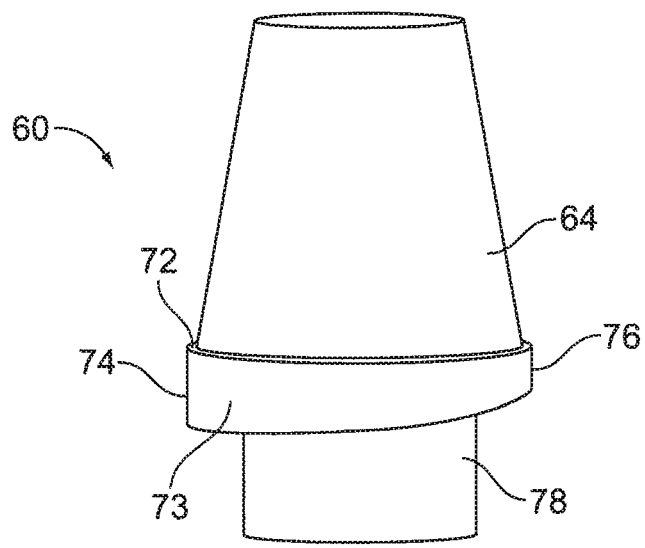
FIG. 7 is a lateral view of a post of the plate-form dental implant of FIG. 6.
Figure 8:
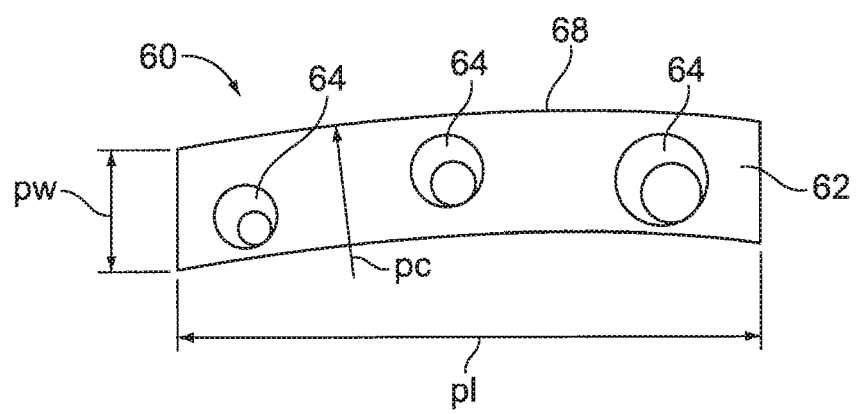
FIG. 8 is a top view of the plate-form dental implant of FIG. 6.

Referring to FIGS. 6-8, a plate-form implant 60 may be made by the process for patient-specific design and manufacturing described above. The implant 60 has an apical blade or plate portion 62 for endosseous attachment and that is partially or substantially made of the porous metal material described herein. Abutments or posts 64 extend coronally from the plate portion 62 to support prosthesis 66 such as crowns, bridges, or dentures. The plate portion 62 is shaped to substantially match the lateral curvature of the jaw of the specific patient, and the posts 64 may be located on the plate portion 62 to correspond to the best locations to support the prosthesis 66. Thus, for example, each post 64 may have a different facial-lingual distance from the facial surface 68 of plate portion 62 (FIG. 8), or may have non-uniform mesial-distal spacing along the plate portion 62.

The porous metal material has unique properties that ideally suit it for the blade implant 60 while eliminating the other disadvantages of the conventional plate-form implant. As mentioned above, the porous nature of the material allows bone to grow through the outer surface of the implant and into the body of the implant. The biologic response to the porous metal material is relatively rapid and the bone in-growth begins to occur quickly. These properties of the porous metal material encourage strong osseointegration rather than fibrous encapsulation.

On the plate-form implant 60, the length (pl), width (pw), and depth (ph) of the plate portion 62 were all set to correspond to the dimensions of a specific patient's preplanned implantation site (or extraction site if such a cavity already exists). The curvature (pc) of the plate portion 62 is set to substantially match that of the specific patient's jaw. Variations in the depth of the plate portion 62 may be made by one or more recesses 70 set back from an outer surface 71 of the implant 60 to bypass anatomic structures such as nerves or blood vessels on the particular patient.

In order to effectively support the prosthesis 66, the posts 64 may be placed at different angles (from an apical-coronal axis 'a') to maximize aesthetics as well as to properly align with bite forces. In some forms, the post 64 may have a widened portion 73 forming a shelf or margin 72 extending radially outward from a base 78 for supporting the prosthesis 66. In one case, the margin 72 may be offset a uniform distance from the alveolar ridge so that it extends generally linear. Alternatively, the margin 72 may be scalloped (FIG. 6) and the dimensions of the scalloping may be different depending on the side of the post 64. Thus, in the illustrated example, the widened portion 73 may be wider on the facial side 74 than on the lingual side 76 of the post 64. Likewise, the mesial and distal sides of the post 64 may also have different dimensions.

Figure 9:
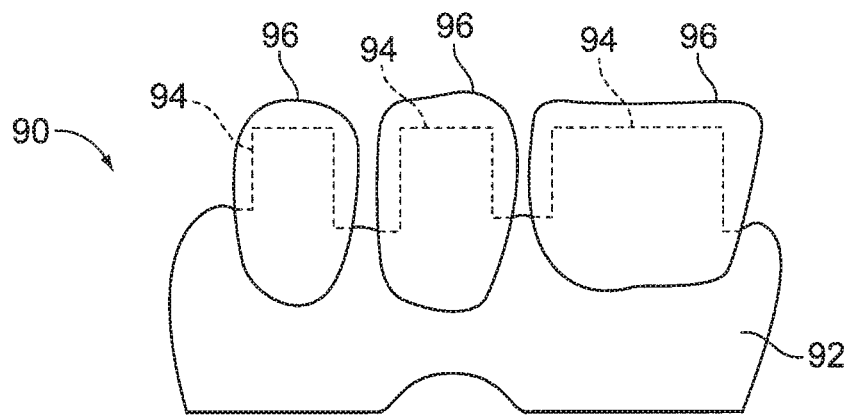
FIG. 9 is a lingual view of a plate-form implant according to another aspect of the present invention.

Referring to FIG. 9, an implant 90, similar to implant 60, has a base portion 92, and posts 94 (shown in dash line) where the base portion 92 is at least partially made of the porous metal material, and may be plate shaped or otherwise. The implant 90 also was made with custom dimensions as with the other implants herein. Here, however, crowns 96 are also designed on the 3D modeling system and fabricated during the design and fabrication process rather than solely by conventional impression mold procedures as described previously. In this example, the patient-specific design process models both the endosseous plate form section and the prosthetic dentition 96 as well as the posts 94. The resulting crowns 96 can be pre-assembled to the implant 90 or may be provided in a kit so that the clinician need only cement or screw retain the prosthesis 96 to the implant 90.

Figure 10:
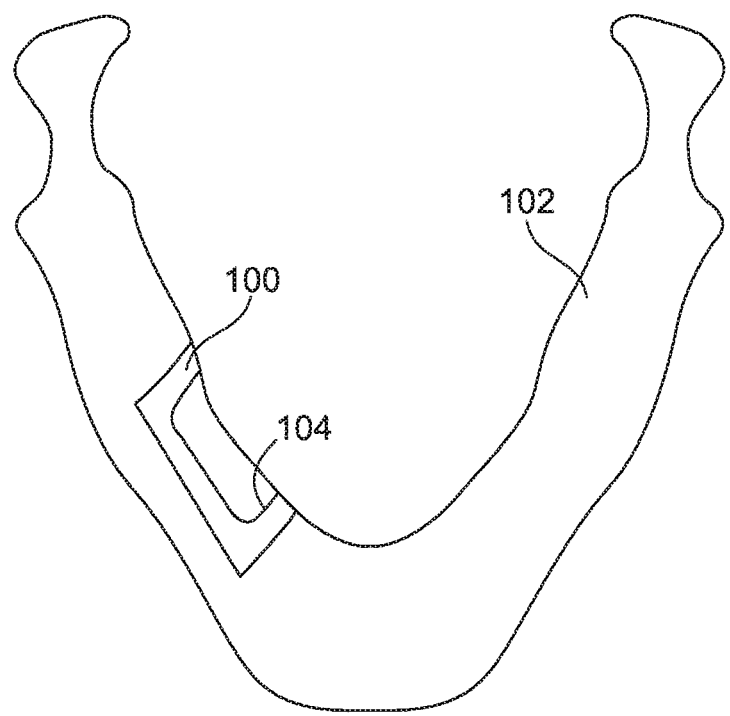
FIG. 10 is an anterior, upper view of a mandible shown with a surgical guide for the placement of the plate-form implants of FIG. 6 or 9.

Referring to FIG. 10, the software used for shaping the implants described above may also be used to form (154 on FIG. 14) a surgical guide 100 by using the same patient-specific data used to design the implant. For example, for guiding the plate-form implant 60 into a mandible 102, saddle shaped surgical guide 100 may be formed and shaped with the CAD/CAM methods described above. The surgical guide 100 is shaped to be located over the particular mesial-distal/facial-lingual location along the mandible 102. The surgical guide 100 also has an opening 104, such as an elongate slot or groove, that is shaped to receive and guide a rotating surgical burr. The groove 104 guides the burr to control the shape and depth of the groove. Optionally, a sleeve, made of metal for example, may fit the groove to further limit lateral motion of the burr to ensure the burr is limited to within the boundaries of the groove 104. Once the surgical guide 100, and sleeve if used, is in place, a trough is cut through the groove 104 and into the bone 102. It will be understood that instead of an elongate groove, opening 104 may be whatever shape is needed including circular openings to form a bore for root-form implants or larger irregular openings for bore-graft type implants described below.

Figure 11:
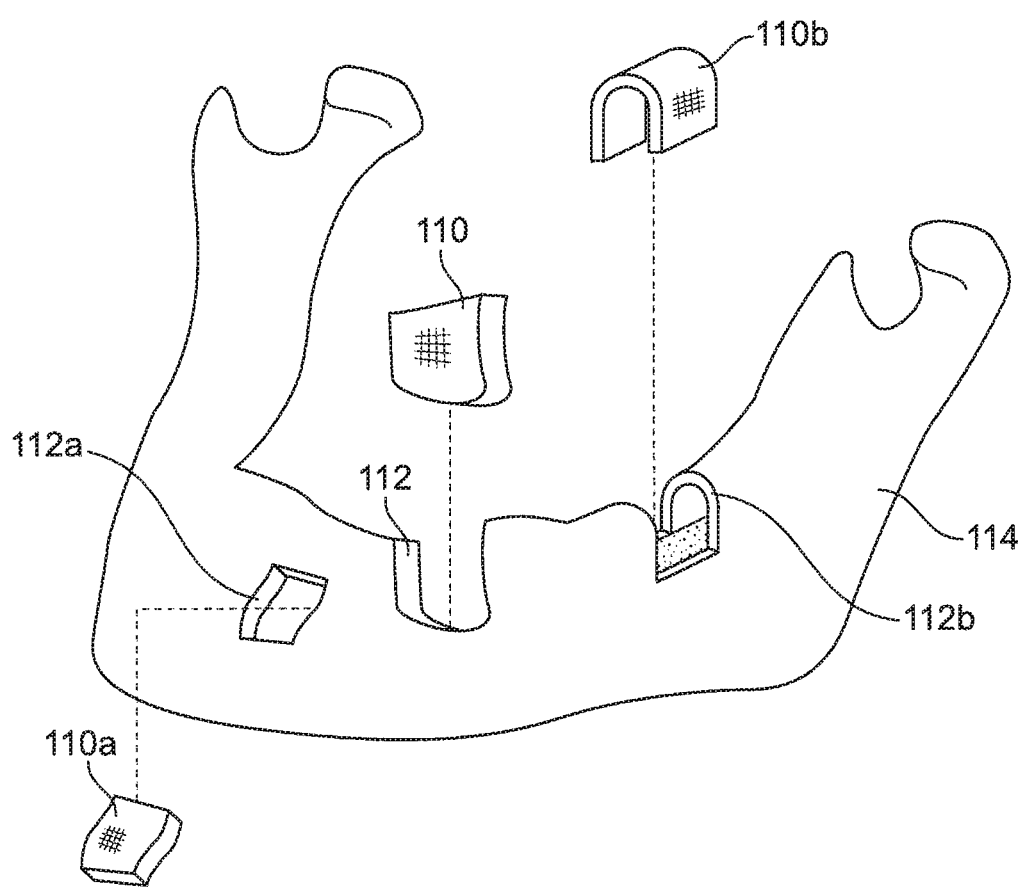
FIG. 11 is an anterior, upper view of a mandible with a porous block implant to be placed in the mandible in accordance with another aspect of the present invention.

Referring to FIG. 11, a porous block 110 of porous material 10 has been formed and shaped by the methods described above to fit the dimensions of a particular defect site 112 on bone 114. Porous block 110 is a non-edentulous, alveolar ridge implant to reinforce decayed alveolar but be covered by a non-anchored section of a denture or bridge, for example. The porous block 110 fits the site 112 better than a hand shaped block and eliminates the need for an additional surgery to harvest bone. Also, typically when a bone graft is placed at a site it must be allowed to heal preferably before the area receives any significant loading and placement of the denture or bridge over the area. Here, however, the improved fit of the patient-specific porous block 110 and the unique properties of the porous metal material permit immediate restoration.

It will be appreciated that the porous block may be formed and shaped into many different shapes, as needed. For example, a more plate shaped porous block 110a may be used to fill a shallow or flat defect site 112a, or a generally saddle shaped porous block 110b may be used to build up reduced ridge areas 112b.

By another alternative, porous block 110 is one of a set of blocks with pre-set dimensions where each block has different dimensions to address a specific anatomical condition. In the illustrated example, each block may be shaped to fit a particular area of a mandible or maxilla. Thus, one block might be dimensioned to build-up the alveolar ridge while another block might be dimensioned to build up the alveolar margin on the mandible, and so forth. Of course a single block may be dimensioned for multiple positions on the mandible or maxilla. In this case, the patient is scanned as described above to determine the dimensions of the implantation site. Then, the pre-set implant that is the best fit to the dimensions of the implantation site is selected for use.

In one form, the blocks are provided without integral abutments so that the practitioner has the option to use each block to support a prosthesis or position the block where it does not support a prosthesis. When support is desired, the block may have a bore to receive a post or the post may be attached to the block as described above for the plate-form implant. It will be appreciated that such pre-dimensioned blocks, or units of blocks, can be provided for any of the embodiments described herein.

The implants described so far are designed to treat tooth loss and bone loss of the alveolar ridge due to tooth decay, bone atrophy, and minor injury. The same patient-specific design and manufacturing process as described above can also be used to shape porous metal implants that repair more severe bone loss due to traumatic injury such as from automobile accidents, severe diseases, and cancer that can result in large quantities of bone being lost and most or all the teeth being lost.

Figure 12:
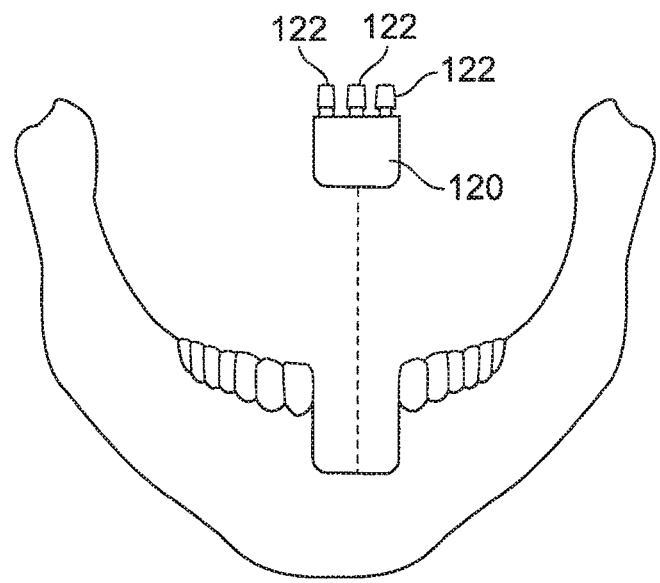
FIG. 12 is an anterior view of a mandible and a multi-tooth, alveolar ridge implant according to another aspect of the present invention.

Referring to FIG. 12, a patient-specific porous metal block 120 has integral posts 122 to support tooth prosthetics. Similar to implant 60, the post 122 and prosthetic dentition can be modeled using the same scan information used to create the block 120 and can be provided pre-assembled or in a kit with the bone grafting implant 120. Here, however, a much larger section of the mandible is replaced or repaired including, for example, areas inferior to the alveolar margin, and as inferior as, or forming, the mental foramen, mental protuberance, or any other part of the mandible.

Figure 13:
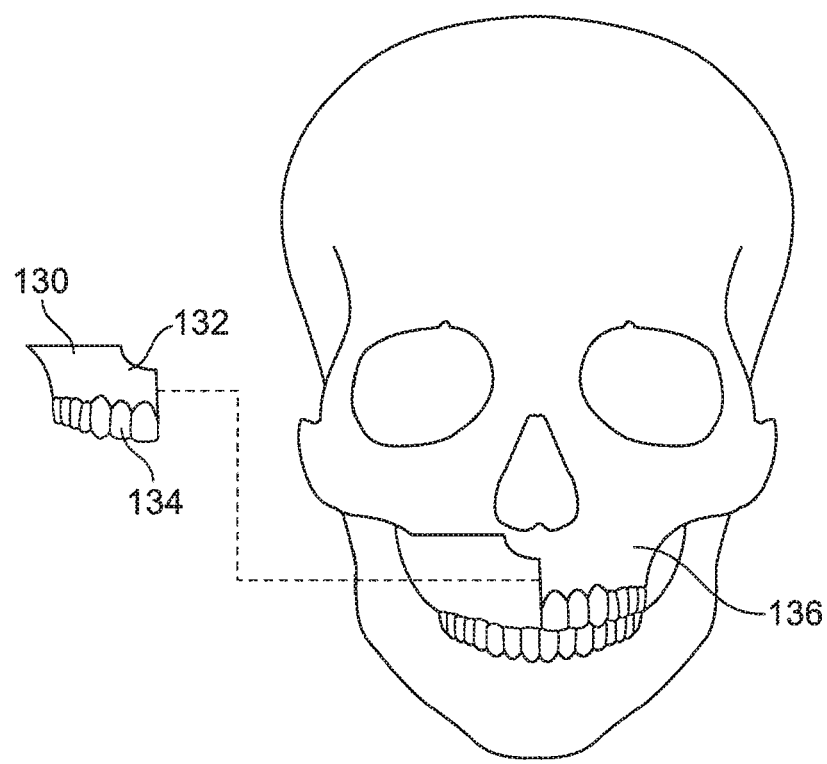
FIG. 13 is an anterior view of a skull and a maxillary, multi-tooth implant according to another aspect of the present invention.

Referring to FIG. 13, porous metal block 130 may be shaped using the same patient-specific design and manufacturing processes as described above. In the illustrated example, block 130 is an implant 132 used to repair a large section of the maxillo-facial area 136 of the skull. In this example, the implant includes prosthetic dentition 134.

Figure 17:
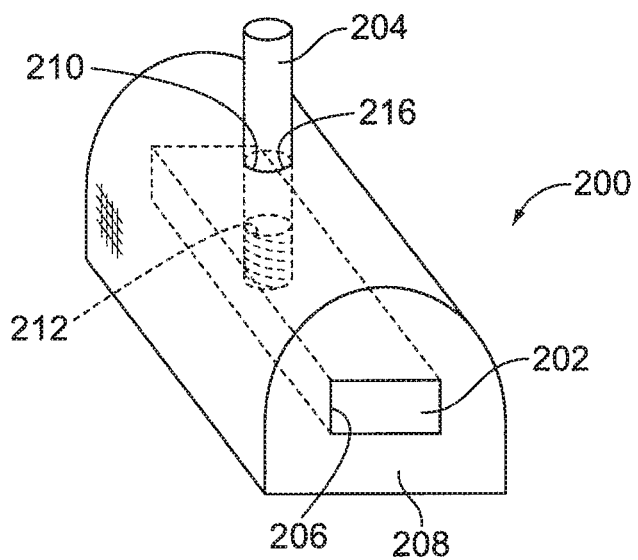
FIG. 17 is a perspective view of an alternative implant in accordance to another aspect of the invention.

Referring to FIG. 17, various metal inserts can be placed into the porous construct to join multiple sections of the porous or solid material. For example, a female threaded insert or anchor member 202 can be press fit into a porous body or block 200 to hold a post 204 on which at least one tooth crown may be fastened or supported thereon. In one form, a hole or window 206 extends from an outer surface 208 of the porous block 200 and the threaded insert is placed in the window while the post 204 is placed through a cavity or bore 210 perpendicular to the window. The post 204 is then threaded to the threaded bore 212 on the insert 202. It will be appreciated that either the post 204 or insert 202 can have the female threads while the other has male threads. It will also be appreciated that instead of a window, the insert 202 could be entirely embedded within the porous block by forming the porous block around the insert.

Figure 18:
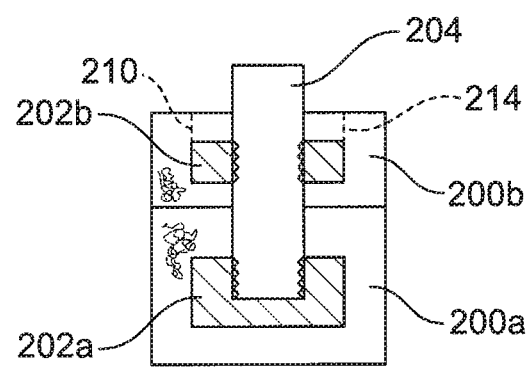
FIG. 18 is a side cross-sectional view of yet another alternative implant in accordance to another aspect of the invention.

Referring to FIG. 18, in another form, multiple pieces of porous material 200a and 200b, each with the window 206 can be secured to each other by first placing the first insert 202a and joining it to post 204. The second porous piece 200b is then inserted on the post 204 and secured to the post by a second female threaded insert 202b. Such a construct of multiple porous blocks and solid sections would allow some variability in the positioning of the crown retaining posts which may be necessary to achieve optimal prosthetic placement of the tooth crowns. Variability in placement would allow the crown to be slightly shifted based on the occlusion of the patient.

It will also be understood that an insert or anchor member 214 may extend to the outer surface of the porous body 200 forming the opening 216 of the cavity 210. So configured, the post 204 is still received by cavity 210 (shown in dash lines on FIG. 18). Here, post 204 only engages the anchor member 202 without engaging porous body 200.

Finally, it will be understood that the post or member 204 may be provided only to secure the porous bodies to each other rather than also support a prosthetic tooth. In such a case, post 204 may not extend out of the porous body.

While this invention may have been described as having a preferred design, the present invention can be further modified within the spirit and scope of this disclosure. This application is therefore intended to cover any variations, uses, or adaptations of the invention using its general principles including non-dental bone areas. Further, this application is intended to cover such departures from the present disclosure as come within known or customary practice in the art to which this invention pertains and which fall within the limits of the appended claims.

What is claimed is:

1. A patient-specific bone implant configured for a bone defect of a patient, the patient-specific bone implant being formed by:
   determining anatomical information of an area of the patient that includes the bone defect, including obtaining the dimensions of the bone defect;
   generating a digital model of at least the dimensions of the bone defect based on the anatomical information;
   planning a three dimensional implant model using virtual structures generated in the digital model, the three dimensional implant model including mathematical representations of a surface of the bone defect;
   providing a block of porous metal material including a core material at least partially coated with a biocompatible metal material;
   shaping the block of porous metal material based on the mathematical representations of the bone defect into the patient specific-bone implant, wherein a body of the patient-specific bone implant has an outer surface sized and shaped to match the dimensions of the bone defect based on the mathematical representations of the bone defect surface, wherein at least a portion of the body has an irregular shape to match the surface of the bone defect, and wherein at least a portion of the outer surface of the body is porous such that the outer surface includes void space when the patient specific bone implant is implanted in a mouth of the patient;
   wherein the patient specific-bone implant comprises:
   a body portion comprising:
     a conical anchor portion at an apical end of the implant;
     an irregular shaped portion connected to the conical anchor portion, the irregular shaped portion including the irregular shape and shaped to accommodate one or more of a nerve location, sinus cavity or tooth root of the area of the patient; and
     a bore extending into only the irregular shaped portion; and
   a collar portion threaded into the bore at a coronal end of the body portion the collar portion having a prosthetic interface with a coronal cavity;
   wherein the block of porous metal material includes a gradation of pore size such that pores are larger on an apical end and smaller on a coronal end.

2. The implant of claim 1 wherein the patient-specific bone implant is a root-form implant that corresponds to the root of a single tooth and supports at least one prosthesis.

3. The implant of claim 1 wherein the patient-specific bone implant supports more than one prosthesis.

4. The patient-specific bone implant of claim 1 wherein the implant replaces multiple tooth root sockets.

5. The patient-specific bone implant of claim 1 wherein the implant extends apically of the alveolar margin.

6. The implant of claim 1 wherein the digital model includes information on the nerve locations, sinus cavities and tooth roots.

7. The implant of claim 1 wherein the digital model includes information on bone density.

8. The implant of claim 1 wherein the collar portion is fabricated from a material other than the porous material.

9. The implant of claim 1 wherein the coronal cavity has a hexagon shape.

10. The implant of claim 1 wherein the block of porous material is shaped into the shape of the bone defect prior to implantation.

11. The implant of claim 1 wherein the core material is carbon foam, and the biocompatible metal material is tantalum.

12. A patient-specific bone implant configured for a bone defect of a patient, the patient-specific bone implant being formed by:
   determining anatomical information of an area of the patient that includes the bone defect, including obtaining dimensions of the bone defect;
   generating a digital model of an area of the patient including the bone defect, based on the anatomical information;
   planning a three dimensional implant model using virtual structures generated in the digital model;
   providing a block of porous material including a core material at least partially coated with a biocompatible metal; and
   shaping the block of porous material into the patient-specific bone implant based on the three dimensional implant model, wherein the block of porous material includes a gradation of pore size such that pores are larger on an apical end and smaller on a coronal end, wherein a body of the patient-specific bone implant has an outer surface sized and shaped to match the dimensions of the bone defect in the digital model, and the core material of the porous material is a carbon foam at least partially coated with the biocompatible metal before or after shaping the block of porous material, and wherein at least a portion of the outer surface of the body is porous such that the outer surface includes void space when the patient specific bone implant is implanted in a mouth of the patient.

13. The patient-specific bone implant of claim 12 wherein the biocompatible metal is tantalum.

14. The patient-specific bone implant of claim 12 wherein the implant is a root-form implant that corresponds to the root of a single tooth and supports at least one prosthesis, the root-form implant comprising:
   a conical anchor portion at an apical end of the block of porous material;
   a prosthetic interface portion coupled to a coronal end of the block of porous material; and
   a body portion comprising the coronal end of the block of porous material, the body portion having an irregular shape to accommodate one or more of a nerve location, sinus cavity or tooth root of the area of the patient.

15. The implant of claim 14 wherein the prosthetic interface portion is fabricated from a material other than the porous material.

16. The patient-specific bone implant of claim 12 wherein the implant supports more than one prosthesis.

17. The implant of claim 12 wherein the patient specific bone implant has an irregular shape to match the surface of the bone defect.

* * * * *

UNITED STATES PATENT AND TRADEMARK OFFICE
CERTIFICATE OF CORRECTION

PATENT NO. : 9,707,058 B2  
APPLICATION NO. : 12/501163  
DATED : July 18, 2017  
INVENTOR(S) : Bassett et al.

Page 1 of 1

It is certified that error appears in the above-identified patent and that said Letters Patent is hereby corrected as shown below:

In Column 12, Line 51, In Claim 1, after "portion", insert --,--

Signed and Sealed this  
Seventh Day of August, 2018

Andrei Iancu  
*Director of the United States Patent and Trademark Office*